United States Patent [19]
Hossain et al.

[11] Patent Number: 5,657,363
[45] Date of Patent: Aug. 12, 1997

[54] METHOD AND APPARATUS FOR DETERMINING THE THICKNESS AND ELEMENTAL COMPOSITION OF A THIN FILM USING RADIOISOTOPIC X-RAY FLUORESCENCE (RXRF)

[75] Inventors: Tim Z. Hossain, Austin; John K. Lowell, Round Rock, both of Tex.

[73] Assignee: Advanced Micro Devices, Inc., Sunnyvale, Calif.

[21] Appl. No.: 541,876

[22] Filed: Oct. 10, 1995

[51] Int. Cl.$^6$ .................................................. G01N 23/223
[52] U.S. Cl. ........................................ 378/45; 378/44
[58] Field of Search ................................ 378/44, 45, 46, 378/50

[56] References Cited

U.S. PATENT DOCUMENTS 3,688,110 8/1972 Severance ........................... 378/46

*Primary Examiner*—David P. Porta
*Attorney, Agent, or Firm*—Kevin L. Daffer; Conley, Rose & Tayon

[57] ABSTRACT

A method and apparatus is presented which applies X-ray fluorescence spectrometry techniques to the problem of determining the elemental composition and thickness of multi-layer structures formed upon a semiconductor substrate. The resulting method and apparatus allows fast, accurate, non-contact, non-destructive, single-measurement determination of the compositions and thicknesses of each thin film on a surface of a measurement sample. Primary X-ray photons emitted by two radioisotopic X-ray sources following defined X-ray paths are incident upon a measurement sample. If the primary X-ray photons have sufficient energy, atoms in the exposed surface of the measurement sample will absorb the energies of the incident primary X-ray photons and emit secondary X-ray photons with characteristic energy levels. Secondary X-ray photons following paths within a defined detection space will reach a sensing face of a lithium-drifted silicon detector and will be detected and counted by a measurement system. The elemental composition of a thin film on an exposed surface of a measurement sample may be determined from the characteristic energy levels of the secondary X-ray photons emitted by the atoms in the thin film. The areas under all corresponding peaks in a graph of the number of secondary X-ray photons detected in predetermined energy ranges (i.e., counts) versus the predetermined energy ranges are directly proportional to the thickness of the thin film.

14 Claims, 7 Drawing Sheets

Schematic of the RXRF Design

METHOD AND APPARATUS FOR DETERMINING THE THICKNESS AND ELEMENTAL COMPOSITION OF A THIN FILM USING RADIOISOTOPIC X-RAY FLUORESCENCE (RXRF)

BACKGROUND OF THE INVENTION

1. Field of the Invention

This invention relates to semiconductor wafer fabrication, more specifically to a non-intrusive apparatus and method for measuring the thickness and elemental composition of a thin film formed on a semiconductor substrate using radioisotopic X-ray fluorescence (RXRF).

2. Description of the Relevant Art

The fabrication of devices in and on a semiconductor substrate generally employs numerous processing steps. The basic processes involved include layering, patterning, doping, and heat treatments. Layering is the process of adding thin layers to the surface of a semiconductor substrate. Thin layers are typically added to the surface of a semiconductor substrate by a chemical reaction with the surface material or by deposition. Layers of metals such as aluminum, tungsten, and titanium may be deposited on the surface of a silicon substrate using evaporation and sputtering techniques.

As the features of very large scale integration (VLSI) circuits continue to shrink, signal time delays due to the resistance and capacitance of the conductors connecting devices to one another (i.e., interconnects) is becoming an appreciable portion of the total signal time delay. Interconnect cross-sectional areas must typically be reduced, leaving a higher resistive path. The sizes of contact regions, where interconnects are physically coupled to implant areas upon the substrate are also shrinking. In an effort to reduce the resistances of interconnects and improve the reliability of contacts, refractory metals such as tungsten (W), platinum (Pt), titanium (Ti), tantalum (Ta), and molybdenum (Mo) are being incorporated into interconnect structures and contact regions.

In contact regions where aluminum abuts the silicon substrate, aluminum and silicon may readily cross-migrate into each other at temperatures above about 450° C. The resulting aluminum-silicon eutectic may penetrate the underlying junction region, effectively short-circuiting the junction and causing device failure. Diffusion barrier layers of refractory metals and alloys such as tungsten (W), titanium (Ti), or titanium-tungsten (TiW) deposited on contact regions prior to aluminum metallization prevent or minimize the eutectic alloying of silicon and aluminum during subsequent heating steps. A first layer of platinum silicide (PtSi$_2$) is often formed on the exposed silicon prior to TiW deposition. The incorporation of refractory metals and their alloys into contact regions is used to improve contact reliabilities. Layers of refractory metals (and their alloys and silicides) are thus often stacked one upon the other, forming multi-layer metal structures.

The physical dimensions (especially thicknesses) of layers such as refractory metals combined to form barriers, silicides, etc. must be closely monitored to ensure optimal results. The separate and cumulative layering of films upon the substrate surface must be monitored in order to ensure thicknesses fall within allowable limits. Layer thicknesses outside those limits may render an ensuing device inoperable or unreliable. Various methods exist for measuring the thickness of a single layer formed on a silicon substrate. One method utilizes optical techniques which rely on interference phenomenon to determine the thickness of a transparent film on the reflective surface of a silicon substrate. Spectrophotometers typically use a source of ultraviolet light to measure the thickness of thin films on a silicon substrate, and use a source of infrared light to measure the thickness of silicon layers. Ellipsometers measure the amount of rotation a polarized laser light beam experiences as it passes through a thin film. Rotation magnitude is determinate of the thickness and index of refraction of the thin film. Another measurement technique involves resistance measurements across the film to determine the thicknesses of (conductive) metal layers with known lengths, widths, and resistivities. A mechanical test method may also be used, involving a stylus drawn across the film surface to measure the step height (i.e., thickness) of the film sample.

Thickness of thin films cannot, as a general rule, be accurately measured using resistance techniques. Additionally, mechanical measurements bear obvious inaccuracies. Still further, optical measurements are limited to the type of film being measured. Refractory metal films cannot be readily measured using optical techniques alone. Optical ellipsometry must therefore be combined with resistance measurements in order to more accurately determine metal layer thickness. While feasible, metal layer thickness readings using the aforesaid combined technique can only be obtained from a single, relatively thick metal layer generally exceeding 500 angstroms. Thickness of a modern day metal layer is oftentimes less than 500 angstroms.

Generally speaking, present techniques can only measure the thickness of a single metal layer. Measuring the thickness of a composite metal structure formed by stacking several metal layers upon each other requires determining the thickness of each layer individually. Separate single layer structures must be formed at sites laterally displaced from the composite metal structure and from each other. For example, a first layer structure must be formed at a location laterally displaced from the composite structure. The first layer structure is formed at the same time the first layer is added to the composite structure. A second layer structure must be formed at a location laterally displaced from the first layer structure and from the composite structure. The second layer structure is also formed at the same time the second layer is added to the composite structure. This process is repeated for each layer of the composite structure. The thickness of each layer is determined individually using one of the present techniques applied to the separate layer structures. The thickness of a multi-layer metal structure is then determined by summing the single layer thickness measurements of all layers within the multi-layer composite.

Measuring the individual thicknesses of each layer of a multi-layer metal structure thus requires (i) test areas or test wafers separate from the multi-layer composite area or wafer, (ii) formations of separate single layer structures for each component layer of the multi-layer metal structure at the test areas or on the test wafers, and (iii) a separate time consumptive thickness measurement for each component layer. This process is costly in terms of time and materials. An overall thickness determination of the multi-layer composite structure is also highly dependent upon accurate duplicity of the layer formation at the single layer structures and within the multi-layer composite. Further, the accuracy of the determined overall thickness of the multi-level metal structure is highly dependent upon the accuracy of the individual single layer thickness measurements.

It would thus be advantageous to have a method and apparatus allowing fast, accurate, non-contact, non-destructive, single-measurement determination of the thickness of a single layer and, equally important, a multilayer metal structure formed upon a semiconductor substrate.

SUMMARY OF THE INVENTION

The problems outlined above are in large part solved by a method and apparatus capable of rapid, non-intrusive measurement of the thickness of a single layer material of singular elemental species. Moreover, the method and apparatus can rapidly determine the thickness of multiple metal layers formed upon each other without having to measure and extrapolate readings from similarly formed, laterally spaced, single layer components. Measurements are particularly attuned to a metal layer or layers. Candidate metals include aluminum, refractory metals, refractory metal silicides, or any other combination of metals. Based on X-ray fluorescence spectrometry, the method and apparatus described herein are capable of fast, accurate, non-contact, non-destructive single measurement of a multi-layer composite structure. One or more layers within the structure can be obtained without requiring separate formation of single layer structures and the problems associated therewith.

The present method is able to identify elemental metal present in all layers deposited on a surface of a measurement sample. Thus a single layer undergoing a thickness measurement may be made up of a pure metal or any combination of metals. In order to enable layer thickness measurements for component layers of a multi-layer metal structure, the elemental composition of each component layer must be known. From a known composition of each layer, the thicknesses of each component layer and the thickness of the overall multi-layer structure may be determined using a single measurement.

The apparatus provides two radioisotopic X-ray sources which emit primary X-ray photons in all directions. The positions of the radioisotopic X-ray sources in relation to a baffle plate and a measurement sample, along with the size and shape of an aperture in the baffle plate, determine the paths in which primary X-ray photons from the two radioisotopic X-ray sources must follow in order to reach the measurement sample. Primary X-ray photons emitted by the two radioisotopic X-ray sources which follow defined X-ray paths will be incident upon the measurement sample. If the primary X-ray photons have sufficient energy, atoms on and in a surface of a measurement sample exposed to primary X-ray photons will absorb the energies of the incident primary X-ray photons and emit secondary X-ray photons with characteristic energy levels. A detection space is defined by the position of the X-ray detector in relation to the baffle plate and the measurement sample, in addition to the size of the aperture in the baffle plate and the size and shape of the sensing face of the X-ray detector. Secondary X-ray photons which follow paths within the defined detection space will reach a sensing face of the X-ray detector and will be detected and counted by a measurement system.

Broadly speaking, the method of the present invention contemplates determining the thickness and/or elemental composition of a thin film on an exposed surface of a measurement sample. First, the exposed surface of the measurement sample is subjected to primary X-ray photons having sufficient energy to cause the atoms on and in the exposed surface of the measurement sample to emit secondary fluorescent X-ray photons. The energy spectrum is divided into a plurality of specific energy ranges, and a measurement system counts the number of secondary fluorescent X-ray photons detected within each specific energy range. The counting step is performed for a predetermined amount of time.

A graph of the number of secondary fluorescent X-ray photons detected within each specific energy range versus the specific energy ranges is then plotted. Peaks occur in the graph, centered around characteristic fluorescent X-ray photon emission energy levels characteristic of the measurement sample. The elemental composition of the thin film is then determined from the fluorescent X-ray photon emission energy levels of the measurement sample atoms.

Thickness of the thin film is also determined from information conveyed by the peaks in the graph of the number of secondary fluorescent X-ray photons detected within each specific energy range versus the specific energy ranges. The area under corresponding peaks in the graph is directly proportional to the thickness of the thin film receiving primary X-ray photons. The areas under the peaks in the graph are calculated. Calibration data is then be applied to the area information to determine the thickness of the thin film.

BRIEF DESCRIPTION OF THE DRAWINGS

Other objects and advantages of the invention will become apparent upon reading the following detailed description and upon reference to the accompanying drawings in which.

Figure 1:
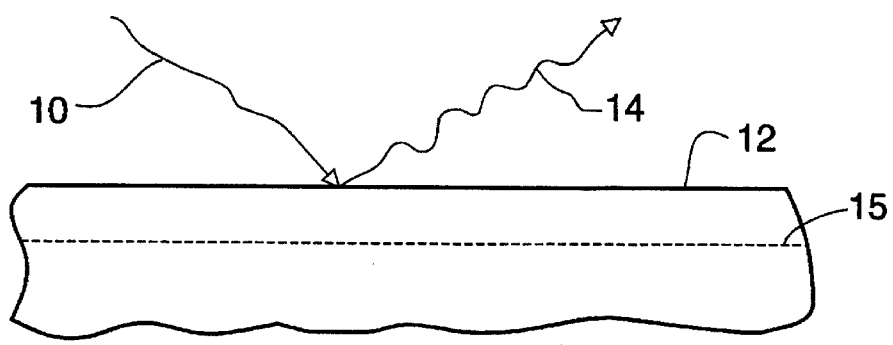
FIG. 1 shows a primary X-ray photon incident upon a target material, and a resulting secondary X-ray photon being emitted by the target material.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The X-ray region of the electromagnetic spectrum gives rise to electromagnetic phenomena not measurable with optical techniques. The X-ray region of the electromagnetic spectrum includes frequencies from $1.0 \times 10^{17}$ Hz to $1.0 \times 10^{21}$ Hz. X radiation displays familiar wave characteristics such as refraction, polarization, diffraction, and scattering. Reflection in the X-ray region occurs only at very low angles of incidence.

X-ray fluorescence spectrometry is known in its application to elemental analysis. When electrically charged particles with sufficient energy strike a target material, X-ray photons are produced. Plotting the number of X-ray photons produced with a given wavelength in a given unit allows determination of a spectral pattern characteristic of the target material. Such a spectral pattern includes intensity peaks characteristic of the target material superimposed on a background X-ray radiation continuum.

Figure 2A:
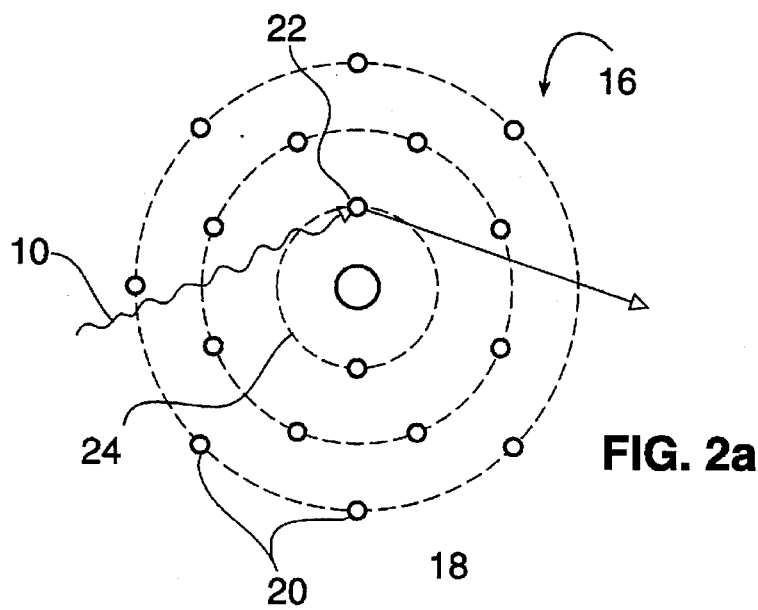
FIG. 2a shows the primary X-ray photon of FIG. 1 impacting an atom of the target material, and the resulting ejection of an electron from the innermost K electron shell of the atom.
Figure 2B:
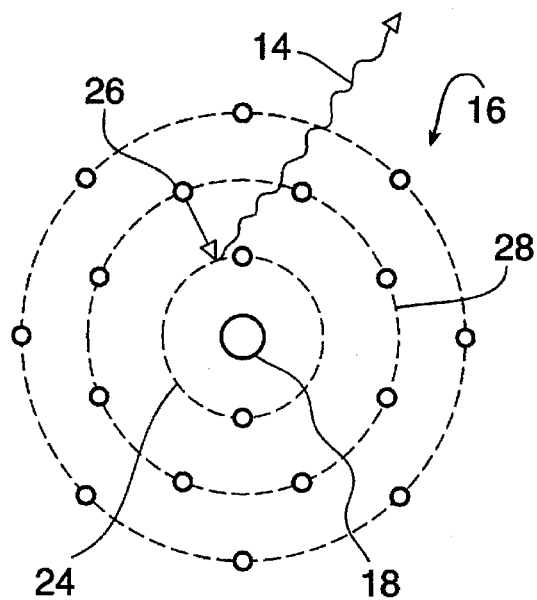
FIG. 2b shows an electron in the L electron shell of the atom of the target material of FIG. 2a filling the vacancy created in the K electron shell, and the simultaneous emission of the secondary X-ray photon.

FIGS. 1, 2a, and 2b will be used to describe in general how X-ray fluorescence occurs within the realm of the present invention. FIG. 1 indicates a primary X-ray photon 10 incident upon a target material 12, and a resulting secondary X-ray photon 14 being emitted from target material 12. X-ray photon absorption and emission occur at the atomic level. FIG. 2a shows an atom 16 of target material 12. In the simple atomic model shown, atom 16 has a nucleus 18 surrounded by electrons 20 at different discrete distances from nucleus 18 called electron shells. A given electron shell has a binding energy level equal to the amount of energy required to remove an electron from the electron shell. The binding energy level of an electron shell is inversely proportional to the distance of the electron shell from the nucleus. The innermost electron shell of an atom is called the K shell, and has the highest binding energy level associated with it. In FIG. 2a, K-shell electron 22 is located in K shell 24.

FIG. 2a also shows primary X-ray photon 10 impacting atom 16 within a target material 12. If the energy level of primary X-ray photon 10 (E) is greater than the binding energy level of a K shell 24 ($\phi_K$) the entire energy of primary X-ray photon 10 is absorbed by atom 16, and one of the electrons in K shell 24 is ejected from atom 16 of target material 12. As depicted in FIG. 2a, K-shell electron 22 is ejected from atom 16 after primary X-ray photon 10 is absorbed by atom 16 of target material 12. K-shell electron 22 is ejected with a kinetic energy of (E-$\phi_K$).

With a vacancy in K shell 24, atom 16 of target material 12 is energetic and unstable. The most probable stabilization mechanism is the filling of the vacancy in K shell 24 by an electron located in an electron shell with a lower binding energy level. As shown in FIG. 2b, an L-shell electron 26 in L shell 28, farther from nucleus 18 than K shell 24, may fill the vacancy in K shell 24. As L-shell electron 26 fills the vacancy in K shell 24, atom 16 may simultaneously emit secondary X-ray photon 14 with energy ($\phi_K-\phi_L$), where $\phi_L$ is the binding energy level of L shell 28. With a vacancy now in L shell 28, ionized atom 16 of target material 12 is more stable and less energetic.

X-ray fluorescence spectrometry permits examination of a target material from the surface of the target material down to a maximum escape depth of secondary X-ray photons. An escape depth 15 of secondary X-ray photon 14 is illustrated in FIG. 1. X-ray fluorescence spectrometry techniques typically allow determination of elemental compositions for materials with atomic numbers greater than 11.

Figure 3:
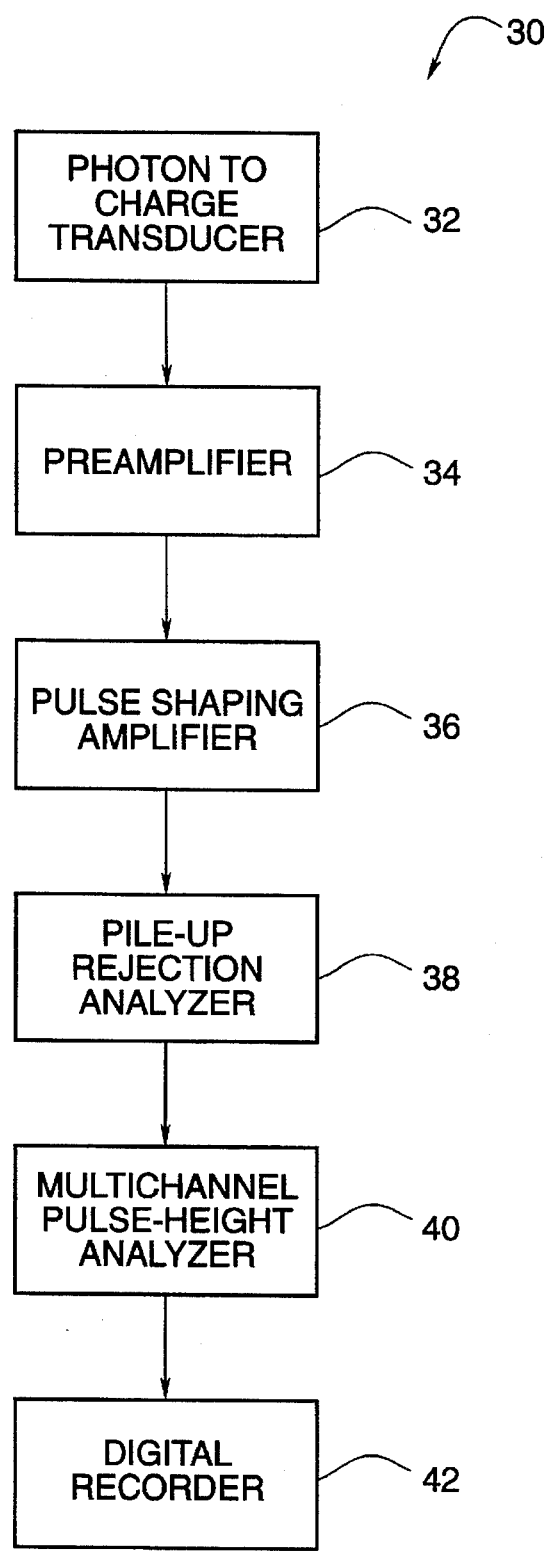
FIG. 3 is a block flow diagram of an X-ray fluorescence measurement process.

Through X-ray fluorescence spectrometry, secondary X-ray photons emitted by a target material may be detected. FIG. 3 shows a block diagram of a measurement system of a typical X-ray fluorescence spectrometer. A photon-to-charge transducer 32 converts the energy of a detected X-ray photon into an electrical charge pulse. The amount of charge produced by photon-to-charge transducer 32 is proportional to the energy level of the detected X-ray photon. A preamplifier 34 converts charge pulses produced by photon-to-charge transducer 32 into high amplitude voltage pulses. A pulse-shaping amplifier 36 provides additional amplification and eliminates much of the "tail" of the voltage pulse occurring after the pulse peak.

The possibility exists that two secondary X-ray photons may arrive at the photon-to-charge transducer 32 at nearly the same time. When this occurs, a pulse of spuriously high amplitude may be produced. A pile-up rejection analyzer 38 eliminates pulses with such spuriously high amplitudes.

A multichannel pulse-height analyzer 40 converts analog pulse height information into a corresponding digital value, and sends the digital pulse height value to a digital recorder 42. Digital recorder 42 has a memory subsystem, and memory locations within this memory subsystem are associated with ranges of pulse height values. Upon receiving a digital pulse height value from pulse-height analyzer 40, digital recorder 42 increments the contents of the corresponding memory location in the memory subsystem by 1. Thus digital recorder 42 keeps track of the number of pulses with certain heights occurring within predetermined pulse height ranges (i.e., the number of detected X-ray photons with energy levels within predetermined energy ranges). The occurrence values associated with predetermined ranges and stored in memory locations of the memory subsystem are called "counts".

X-ray fluorescence spectrometry measurements are conducted over fixed time intervals. After a predetermined amount of time has elapsed, digital recorder 42 ceases storing digital pulse height information. The counts stored in memory locations of the memory subsystem of digital recorder 42 may then be retrieved and analyzed.

Figure 4:
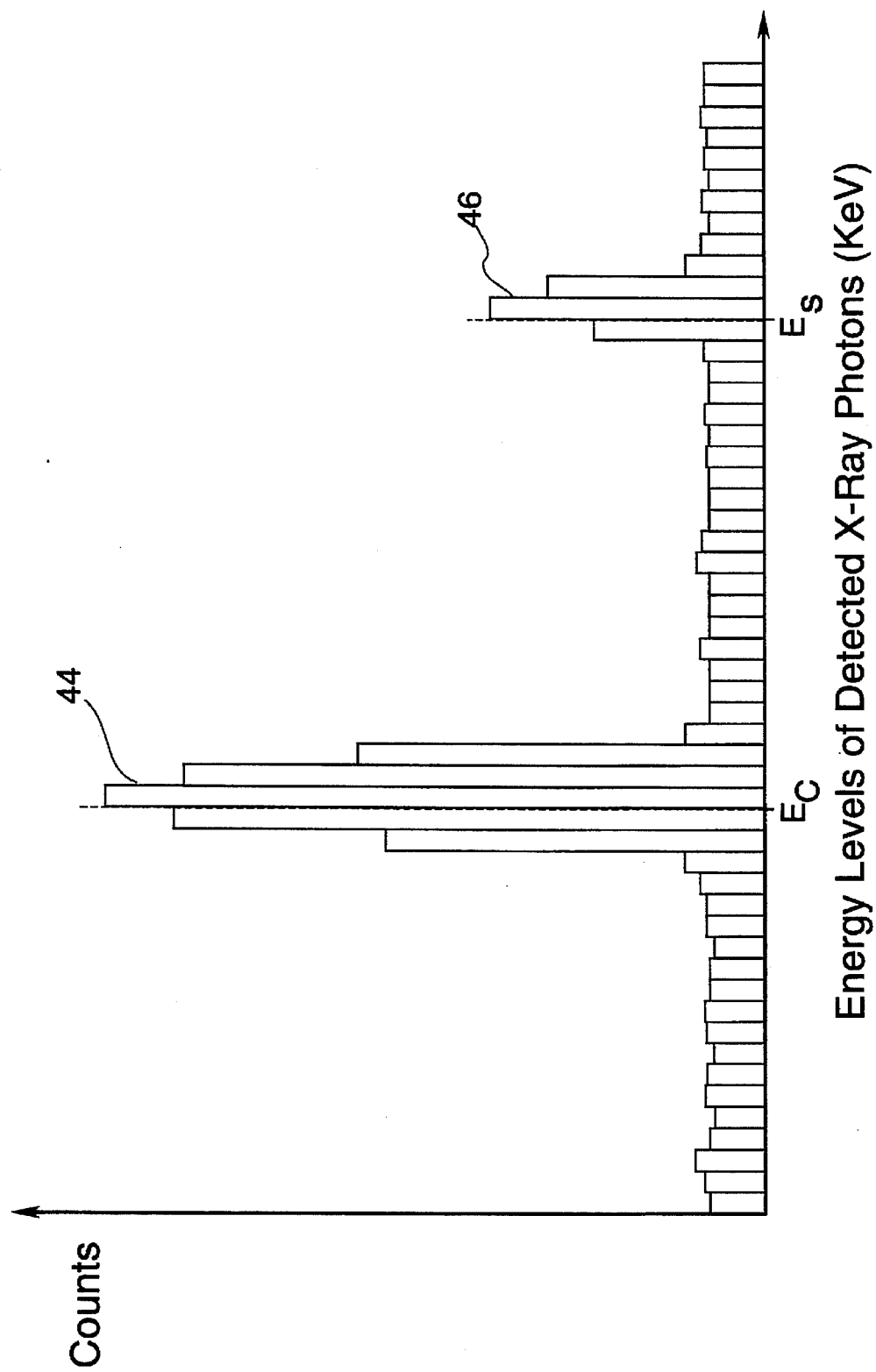
FIG. 4 is a representative graph of counts obtained from an X-ray fluorescence spectrometer versus the energy levels of detected X-ray photons.

FIG. 4 shows a representative graph of the counts obtained from an X-ray fluorescence spectrometer versus the energy levels of detected X-ray photons. Such a plot is called a spectral pattern. If a target material is made up of a single element, a single large peak 44 may occur centered around a characteristic emission energy level of the target material, $E_C$. The value of the characteristic emission energy level $E_C$ is the difference in binding energy levels of two electron shells of the target material, and may be used to identify the element composing the target material. A small peak 46 may occur at an energy level $E_S$ (greater than $E_C$) due to scattering of the primary X-ray photons by the target material.

With X-ray photon excitation, the spectral pattern of a target material includes large peaks only at the characteristic emission energy levels of elements making up the target material. The energies of the bombarding primary X-ray photons (i.e., quanta) are completely absorbed, resulting in the lack of a background radiation continuum. (Background X-ray radiation observed in a spectral pattern produced using X-ray fluorescence spectrometry is attributable mainly to scattering of the X-ray photons bombarding the target material). The absence of a background X-ray radiation continuum allows more sensitive measurements to be made using X-ray fluorescence spectrometry.

Sources for X-ray fluorescence spectrometry include X-ray tubes and radioisotope sources. X-ray sources using X-ray tubes offer high output powers, but dissipate large amounts of electrical power in producing X-ray photons. Radioisotope sources produce lower output powers, but are much smaller and lighter than X-ray sources using X-ray tubes and consume no electrical power. Sources with lower output powers may also be placed closer to a sample and a detector in a measuring system. In addition, a key application of the present invention is use within a semiconductor fabrication area. A radioisotopic source is highly desirable inside a semiconductor fabrication area since no maintenance of the primary x-ray source is necessary. Alternatives to radioisotopic sources, such as x-ray tubes, require periodic maintenance. Performing periodic maintenance on such alternative x-ray sources located within a semiconductor fabrication area is difficult and undesirable. Radioisotopes do, however, experience a gradual loss of output power over time with radioactive decay. More information on X-ray fluorescence spectrometry may be found in H. Strobel et al., *Chemical Instrumentation: A Systematic Approach*, 1989, John Wiley & Sons, New York, pp. 723–777 (herein incorporated by reference).

Figure 5:
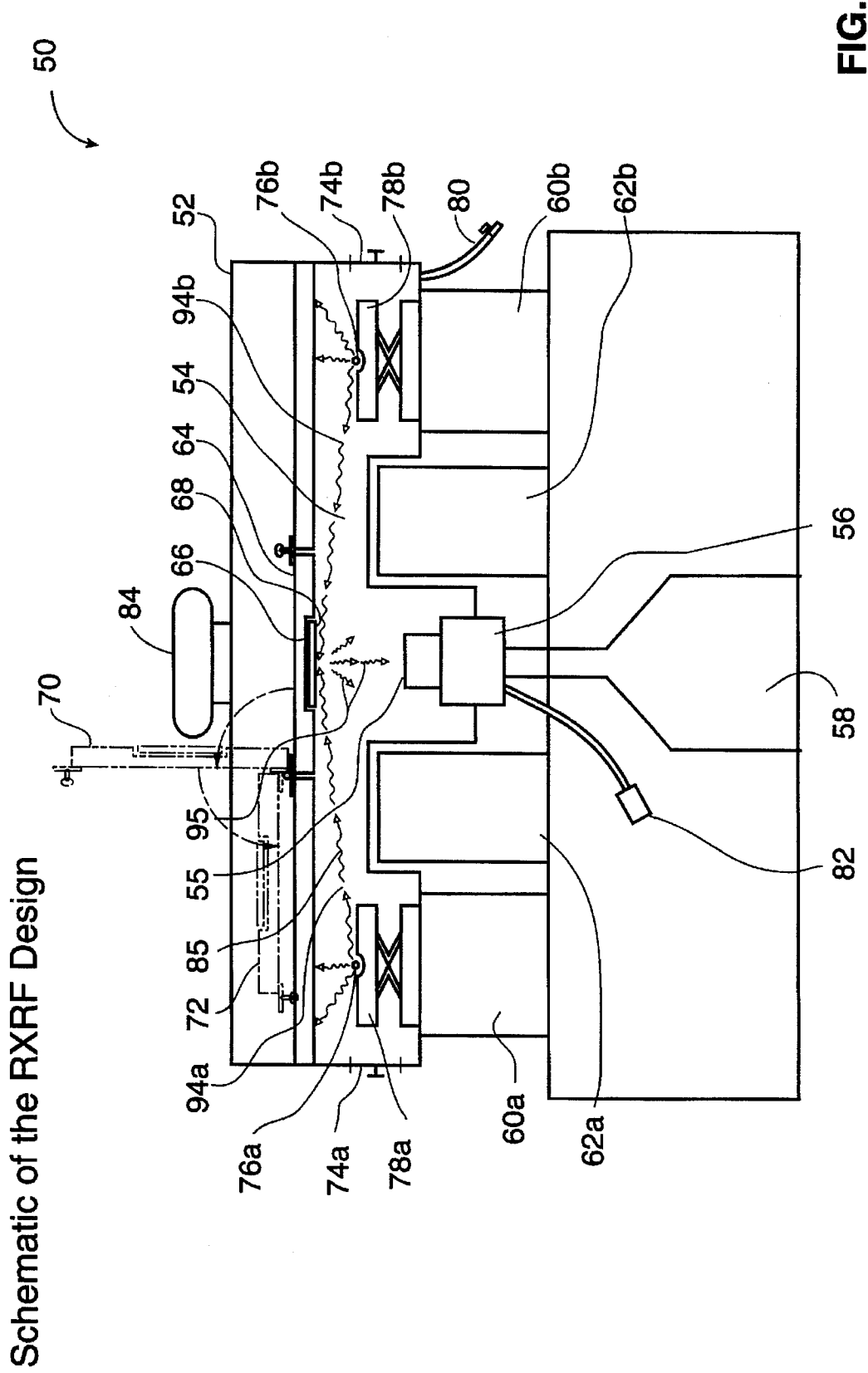
FIG. 5 shows one embodiment of an apparatus for the measurement of thin film thickness using radioisotopic X-ray fluorescence (RXRF)

FIG. 5 shows one embodiment of an apparatus for the measurement of thin film thickness using radioisotopic X-ray fluorescence (RXRF) in accordance with the present invention. Measurement apparatus 50 includes a supporting frame 52, a vacuum chamber 54, a lithium-drifted silicon detector 56, a liquid nitrogen dewar 58, vacuum chamber supports 60a and 60b, and lead shielding units 62a and 62b.

Sample access port 64 may be a hinged door in a top surface of vacuum chamber 54 as shown in FIG. 5. Sample access port 64 has a sample holder 66 for mounting of a measurement sample 68. A seal is formed around sample access port 64 when sample access port 64 is in a closed position, allowing a vacuum to be drawn inside vacuum chamber 54 prior to use.

In the embodiment of FIG. 5, an exposed surface of measurement sample 68 faces downward when undergoing a thickness measurement. Sample access port 64 may be hinged as shown to facilitate the mounting and dismounting of measurement sample 68. Sample access port 64 may be opened to a horizontal position 72 by allowing sample access port to first pass through a vertical position 70. When sample access port 64 is in horizontal position 72, measurement sample 68 faces upward and may be more easily mounted and dismounted.

As shown in FIG. 5, vacuum chamber 54 also has two source access ports 74a and 74b to permit access to radioisotopic X-ray sources 76a and 76b, respectively. Seals are formed around source access ports 74a and 74b when source access ports 74a and 74b are in closed positions, allowing a vacuum to be drawn inside vacuum chamber 54 prior to use.

Radioisotopic X-ray sources 76a and 76b are held in place by source holders 78a and 78b, respectively, within vacuum chamber 54. Vacuum tube with clamp 80 may be connected to a vacuum pump (not shown) in order to evacuate the air from vacuum chamber 54.

A sensing face 55 of a lithium-drifted silicon detector 56 is mounted within vacuum chamber 54 and oriented toward measurement sample 68 in sample holder 66 during use. An electrical cable with connector 82 extends from lithium-drifted silicon detector 56 for connection to an electronic measurement system (not shown). Liquid nitrogen dewar 58 is a container for liquid nitrogen used to cool lithium-drifted silicon X-ray detector 56.

Lithium-drifted silicon detector 56 is a semiconductor p-i-n diode formed when a portion of a p-type silicon disk is doped with n-type lithium. Continuously cooled to about −196° C. with liquid nitrogen to prevent further diffusion of lithium and reverse-biased during use, lithium-drifted silicon detectors are capable of transducing the energy of incident X-ray photons into charge pulses. The amount of charge produced by a lithium-drifted silicon detector is directly proportional to the energy of an incident X-ray photon. Lithium-drifted silicon detectors are commercially available (EGG ORTEC, Oakridge, Tenn.).

Vacuum chamber supports 60a and 60b function as supports for vacuum chamber 54. Lead shielding units 62a and 62b shield lithium-drifted silicon X-ray detector 56 from direct X-ray exposure from radioisotopic X-ray sources 76a and 76b, respectively. A handle 84 at the top of measurement apparatus 50 adds the feature of portability to measurement apparatus 50.

Figure 6:
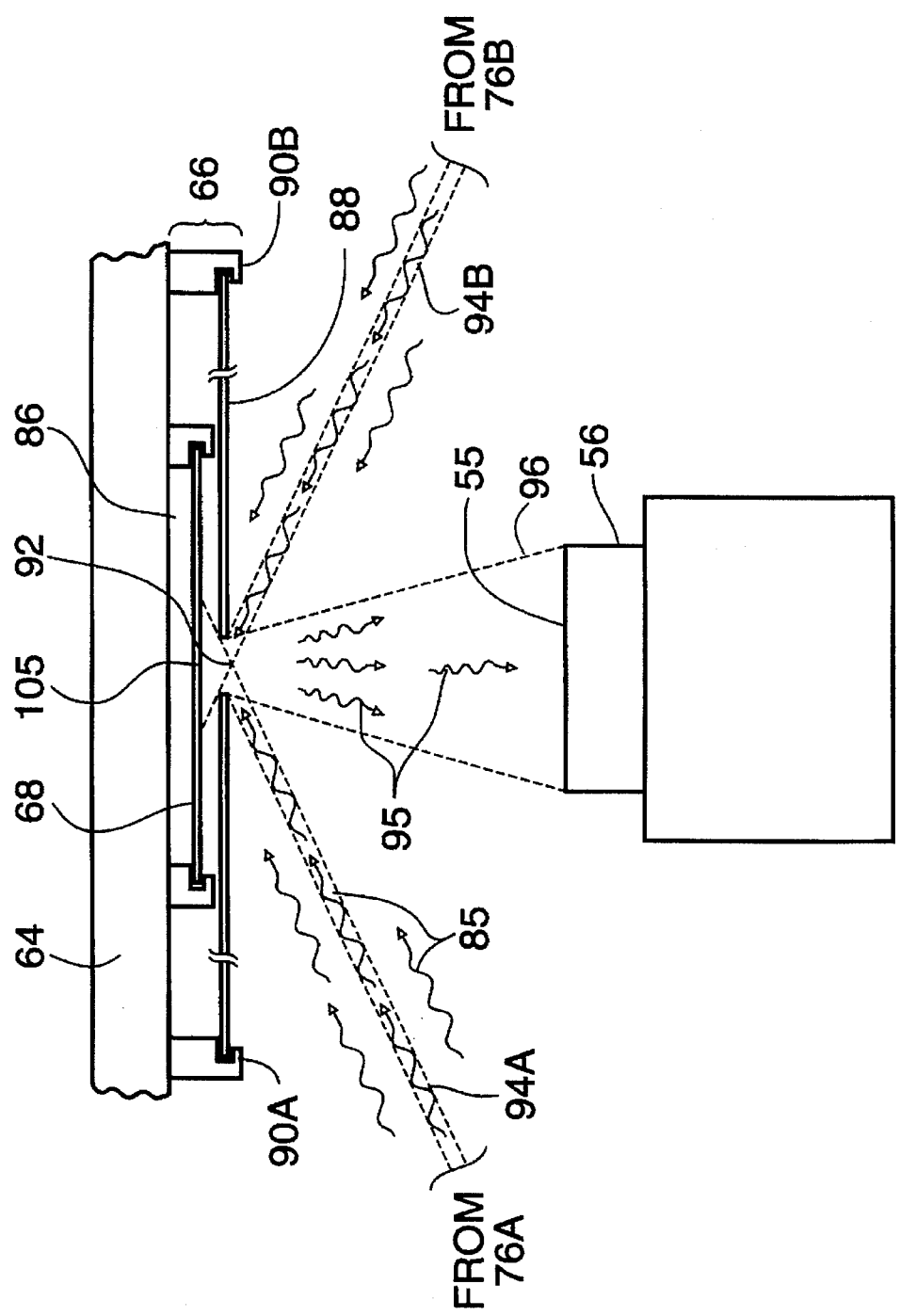
FIG. 6 shows a cross-sectional view of one embodiment of a sample holder within a sample access port of the measurement apparatus of FIG. 5.

FIG. 6 shows a cross-sectional view of one embodiment of sample holder 66 in sample access port 64 of measurement apparatus 50. Here sample holder 66 has been configured to hold a measurement sample consisting of a flat circular plate of semiconductor material (i.e., a semiconductor wafer) and allow a thickness measurement to be carried out on only a small portion of an exposed surface of the semiconductor wafer. Measurement sample 68 is held in a semiconductor wafer clamp assembly 86. A baffle plate 88 is held in a position below measurement sample 68 by two or more baffle plate supports 90. Two baffle plate supports 90a and 90b are shown in FIG. 6. Only X-ray photons which pass through an aperture 92 in baffle plate 88 may reach measurement sample 68.

Wafer clamp assembly 86 may employ retractable mechanical fingers or a vacuum chuck assembly in order to suspend measurement sample 68 above baffle plate 88. In addition, wafer clamp assembly 86 may be a movable stage allowing precise positioning of measurement sample 68 relative to aperture 92 in baffle plate 88.

Baffle plate 88 may be made from a material in which the binding energy levels of inner electron shells are greater than the energy levels of X-ray photons produced by radioisotopic X-ray sources 76a and 76b, or a material which produces secondary X-ray photons at a known energy level distinctly different from those of the target material. This will prevent X-ray photons incident upon the baffle plate from interfering with the measurement.

FIGS. 5 and 6 will now be used to describe the basic method of determining the thickness and/or elemental composition of a thin film on the surface of a measurement sample using measurement apparatus 50. Radioisotopic X-ray sources 76a and 76b may first be positioned on source holders 78a and 78b within vacuum chamber 54 using source access ports 74a and 74b. Electrical cable with connector 82 of lithium-drifted silicon X-ray detector 56 may then connected to an electronic measurement system (not shown), and the electronic measurement system may be activated and initialized.

Sample access port 64 may then be opened to horizontal position 72, and measurement sample 68 mounted in measurement holder 66 of sample access port 64. Sample access port 64 may then be closed, reversing the orientation of the thin film to be measured such that it faces downward and is exposed to the chamber. A vacuum may then be drawn inside vacuum chamber 54 by connecting vacuum tube with clamp 80 to the inlet of a vacuum pump (not shown).

Radioisotopic X-ray sources 76a and 76b emit primary X-ray photons 85 in all directions. The positions of radioisotopic X-ray sources 76a and 76b in relation to baffle plate 88 and measurement sample 68, in addition to the size and shape of aperture 92 in baffle plate 88, determine the paths primary X-ray photons 85 emitted by radioisotopic X-ray sources 76a and 76b must follow in order to reach measurement sample 68. The path from radioisotopic X-ray source 76a which allows primary X-ray photons 85 to reach measurement sample 68 is labeled X-ray path 94a. The path from radioisotopic X-ray source 76b which allows primary X-ray photons 85 to reach measurement sample 68 is labeled X-ray path 94b. Primary X-ray photons 85 which follow other paths do not contribute to the measurement.

Figure 7:
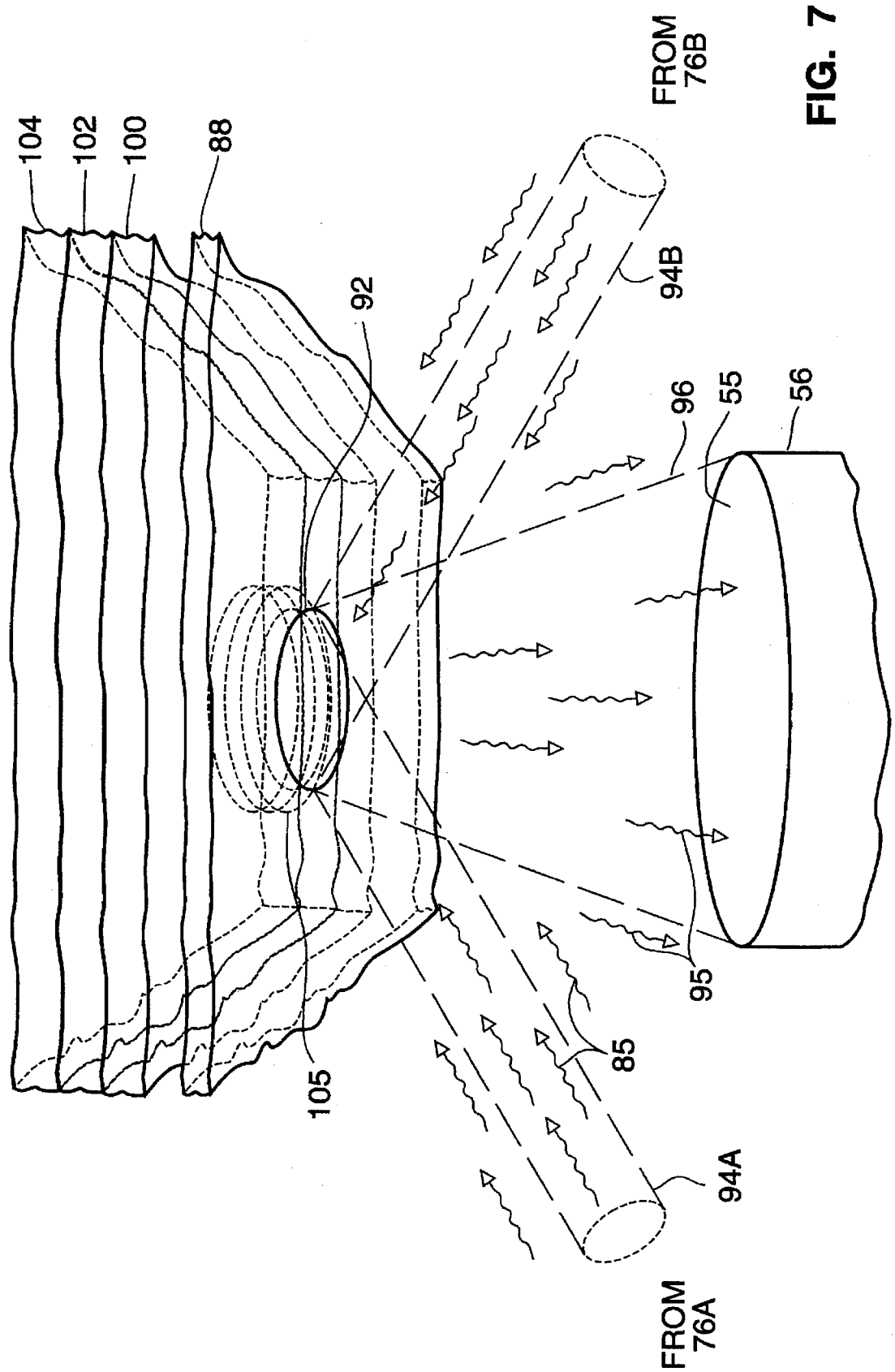
FIG. 7 shows the apparatus of FIG. 5 and how it may be used to determine the elemental compositions and thicknesses of two layer (multi-layer composite) structure formed on semiconductor substrate.

As shown in FIGS. 6 and 7, primary X-ray photons 85 emitted by radioisotopic X-ray sources 76a and 76b which follow X-ray paths 94a and 94b will be incident upon measurement sample 68 in area 105. If primary X-ray photons 85 incident upon measurement sample 68 have sufficient energy, atoms in and on the exposed surface of measurement sample 68 will absorb the energies of the incident primary X-ray photons 85 and emit secondary X-ray photons 95 with characteristic energy levels. A detection space 96 is defined by the position of lithium-drifted silicon X-ray detector 56 in relation to baffle plate 88 and measurement sample 68, in addition to the size of aperture 92 in baffle plate 88 and the size and shape of sensing face 55 of lithium-drifted silicon X-ray detector 56. Secondary X-ray photons 95 emitted by atoms in and on the exposed surface of measurement sample 68 which follow paths within detection space 96 will reach the sensing face 55 of lithium-drifted silicon X-ray detector 56 and will be detected.

It shall be noted that the size and shape of incidence area 105 depends on the size and shape of aperture 92 in baffle plate 88. In addition, the size and shape of incidence area 105 will depend on the positions of radioisotopic X-ray sources 76a and 76b in relation to baffle plate 88 and measurement sample 68. For example, moving radioisotopic X-ray sources 76a and 76b up in a vertical direction such that they become closer to the upper horizontal surface of vacuum chamber 54 increases the size of incidence area 105 on the exposed surface of measurement sample 68. Moving radioisotopic X-ray sources 76a and 76b down in a vertical direction such that they become farther away from the upper horizontal surface of vacuum chamber 54 decreases the size of incidence area 105. Moving baffle plate 88 up in a vertical direction and closer to measurement sample 68 decreases the size of incidence area 105. Moving baffle plate 88 down in a vertical direction and farther from measurement sample 68 increases the size of incidence area 105.

Figure 8:
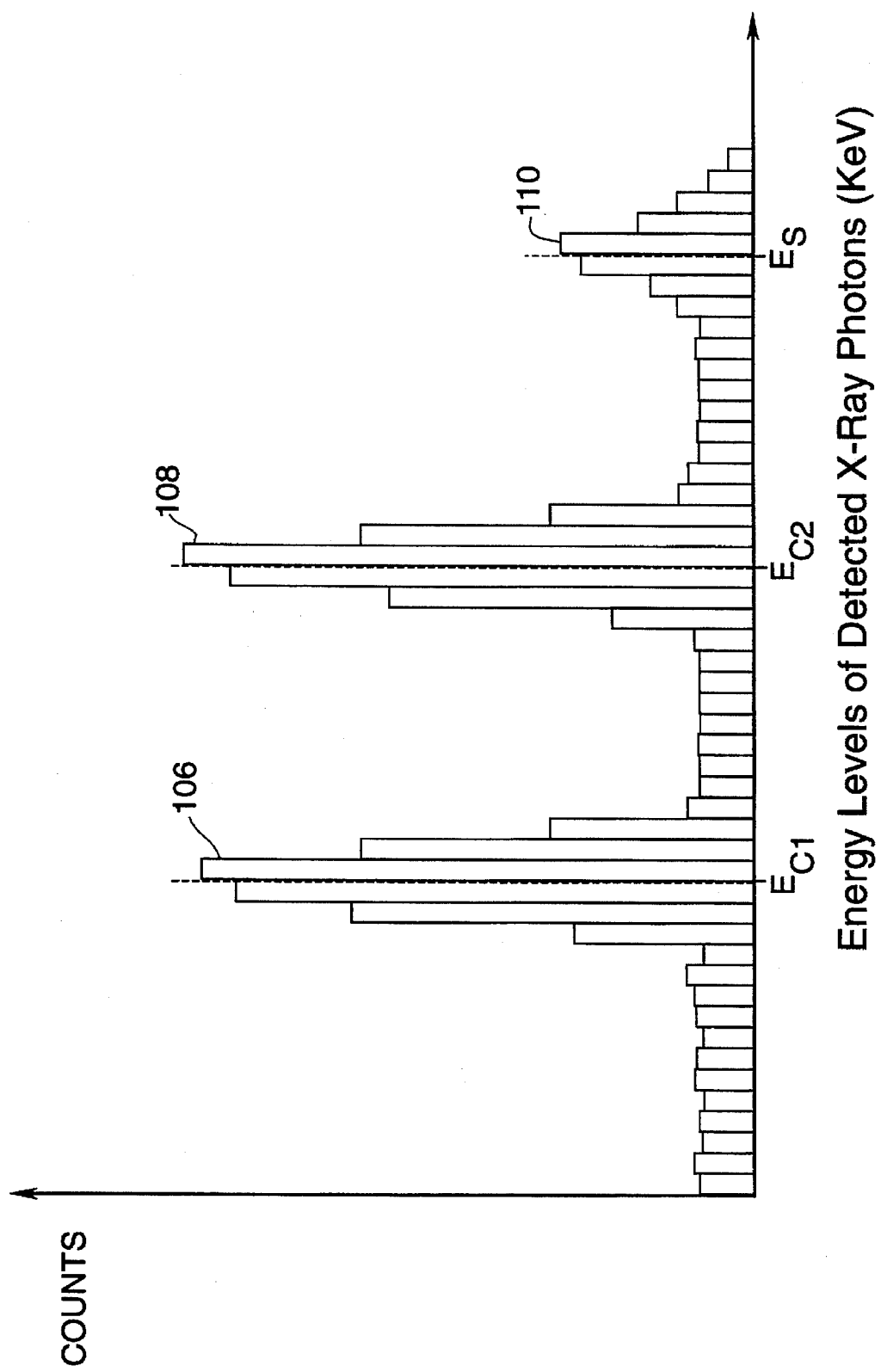
FIG. 8 is a graph of counts obtained from a measurement system connected to the apparatus of FIG. 5 versus predetermined energy ranges of detected X-ray photons for the example of FIG. 7.

FIGS. 7 and 8 will now be used to describe how the method of the present invention may be used to determine the thicknesses of two thin films on an exposed surface of a measurement sample using measurement apparatus 50. As shown in FIG. 7, a first thin film 100 is formed upon a second thin film 102 on an exposed surface of a measurement sample 104. In this example, first thin film 100 is made up of a pure metal (i.e., single metallic elemental species). Second thin film 102 is also made up of a pure metal. The pure metal of second thin film 102 is different than the pure metal of first thin film 100. The combined thicknesses of first thin film 100 and second thin film 102 are less than the escape depth of any secondary X-ray photons generated.

Primary X-ray photons 85 incident upon measurement sample 104 may cause atoms in thin films 100 and 102 on the exposed surface of measurement sample 68 to absorb the energies of the impinging primary X-ray photons and emit secondary X-ray photons 95 with characteristic energy levels. Secondary X-ray photons 95 emitted by atoms in thin films 100 and 102 which follow paths within detection space 96 will reach the sensing face 55 of lithium-drifted silicon X-ray detector 56 and will be detected.

A measurement system connected to the apparatus of FIG. 5 counts the number of secondary fluorescent X-ray photons detected within specific energy ranges in a sampling of the secondary fluorescent X-ray photons emitted by the atoms on and in the exposed surface of the measurement sample. This counting operation is performed for a predetermined amount of time.

FIG. 8 shows a graph of counts of secondary X ray photons detected within predetermined energy ranges versus the predetermined energy ranges. A first large peak 106 is centered around a characteristic emission energy level $E_{C_1}$, and a second large peak 108 is centered around a characteristic emission energy level $E_{C_2}$. Any peaks caused by elements making up measurement sample 104 have been omitted. The values of $E_{C_1}$ and $E_{C_2}$ are characteristic of the atoms making up first thin film 100 and second thin film 102 on the exposed surface of measurement sample 104. Small peak 110 centered around the energy level of the source radiation $E_S$ is due to the scattering of primary X-ray photons by the measurement sample. Note that the energy level $E_S$ associated with scattered primary radiation is higher than energy levels associated with any other peaks in the graph since the energy level of primary X-ray photons must exceed the energy levels of secondary X-ray photons.

Without being bound to theory, it is determined that the number of counts associated with a given thin film is directly proportional to the number of atoms present in the portion to the thin film being measured. The number of atoms present in the portion to the thin film exposed to primary X-ray photons is directly proportional to the thickness of the thin film. Thus the areas under first large peak 106 and second large peak 108 are directly proportional to the thicknesses of associated first thin film 100 and second thin film 102, respectively. Calibration data may be applied to the calculated area underlying the respective count curvature, and the resulting data is determinative of the thicknesses of first thin film 100 and second thin film 102.

A given number of counts is associated with each peak, and each count is associated with a fixed energy range. The area under a given peak may thus be estimated by multiplying the sum of all counts associated with the peak by the fixed amount of energy associated with each energy range. An algorithm can be employed to perform well known numerical integration, of the area under a given peak curvature.

It is noted that because the thicknesses of first thin film 100 and second thin film 102 are the same in the example shown in FIGS. 7 and 8, it is not possible to relate an elemental composition with a particular thin film. The metals making up the thin films may be identified through a look up table. However, it is not possible to associate a given metal with a given layer. Additional information is needed, such as the known elemental composition of one of the two thin films. A known elemental composition of one thin film will allow the operator to make an association of one peak (with corresponding known energy count peak) to an unknown thickness associated with a layer of the other energy count peak. Knowing the elemental composition exclusive to one thin film will allow the operator to determine the elemental composition of the other film. If one thin film had been thicker than the other, however, determinations of the thicknesses and elemental compositions of both thin films would have been possible. The present method and apparatus thereby allows correlation of energy count peak to the determination of elemental composition. Knowing one layer has a single elemental composition allows a determination of the single elemental composition of the other layer as well as the thicknesses of both layers. If needed, this process can be applied to more than two layers, provided compositions of all but one layer is known and that each layer contains a single elemental species.

Application of X-ray fluorescence spectrometry techniques to the problem of determining the thickness of at least one thin film upon a semiconductor wafer has broad based applications in the semiconductor industry. Fast, accurate, non-contact, non-destructive, single-measurement determination of the compositions and thicknesses of each thin film of a multi-layer structure is an important outcome hereof.

The elemental composition of a thin film on an exposed surface of a measurement sample is determined from the characteristic energy levels of the secondary X-ray photons emitted by the atoms in the thin film. The areas under corresponding peaks in a graph of counts obtained from the measurements system versus predetermined energy ranges of detected X-ray photons are directly proportional to the thickness of the thin film. To determine the thickness of a thin film on an exposed surface of a measurement sample, the area under all corresponding peaks in a graph of counts obtained from the measurements system versus the predetermined energy ranges of detected X-ray photons are first calculated. Using calibration data, the thickness of the thin film may then be determined from the areas under the corresponding peaks.

It will be appreciated to those skilled in the art having the benefit of this disclosure that this invention is believed to be capable of fast, accurate, non-contact, non-destructive, single-measurement determination of the elemental compositions and thicknesses of each thin film on a surface of a measurement sample. Furthermore, it is also to be understood that the form of the invention shown and described is to be taken as exempemplary, presently preferred embodiments. Various modifications and changes may be made without departing from the spirit and scope of the invention as set forth in the claims. It is intended that the following claims be interpreted to embrace all such modifications and changes.

What is claimed is:

1. An apparatus for measuring the elemental composition and thin film thickness of a multi-layer sample comprising:
   a plurality of radioisotopic X-ray sources held by a plurality of source holders for producing primary X-ray photons;
   a baffle plate adjacent to the sample positioned between said X-ray sources and said sample, wherein said baffle plate comprises an aperture through which a portion of said primary X-ray photons must travel to become incident upon the sample and through which a portion of secondary X-ray photons emitted from said sample must travel to reach an X-ray detector;
   wherein said aperture is configured to limit the area of said sample which is exposed to said portion of primary X-ray photons;
   wherein said X-ray detector has a sensing face oriented toward said sample and is configured to receive said portion of secondary X-ray photons; and
   a clamp configured to hold said sample and configured to move said sample relative to said aperture so as to adjust the area and location of said sample which is exposed to said portion of primary X-ray photons.

2. The apparatus recited in claim 1, wherein said source holders are configured to adjust the distance between said X-ray sources and said sample.

3. The apparatus recited in claim 1, wherein said plurality of X-ray sources consists of two sources.

4. The apparatus recited in claim 1, wherein said baffle plate is made from a material in which the binding energy levels of inner electron shells are greater than the energy of said primary X-ray photons.

5. The apparatus recited in claim 1, wherein said baffle plate is made from a material which produces secondary X-ray photons at a known energy level distinctly different than the energy levels of secondary X-ray photons emitted by said multi-layer sample.

6. The apparatus recited in claim 1, wherein said X-ray detector comprises a lithium-drifted silicon detector.

7. The apparatus recited in claim 1, further comprising a liquid nitrogen dewar to hold liquid nitrogen used to cool said detector.

8. The apparatus recited in claim 1, wherein said plurality of X-ray sources, said baffle plate, said clamp, and said sensing face are contained within a vacuum chamber.

9. The apparatus recited in claim 8, further comprising a sample holder adapted for mounting of said sample, said sample holder positioned on the underside of a sample access port such that the exposed surface of said sample is oriented downward during use.

10. The apparatus recited in claim 9, wherein said sample access port is attached to a top surface of said vacuum chamber via a hinge in order to facilitate mounting and dismounting of said sample.

11. An apparatus for measuring the elemental composition and thin film thickness of a multi-layer sample comprising:
    a sample holder adapted for mounting of said sample;
    two radioisotopic X-ray sources, held by a plurality of source holders, producing primary X-ray photons, wherein said source holders are configured to adjust the distance between said X-ray sources and said sample;
    a baffle plate adjacent to said sample positioned between said X-ray sources and said sample, wherein said baffle plate comprises an aperture through which a portion of said primary X-ray photons must travel to become incident upon said sample and through which a portion of secondary X-ray photons emitted from said sample must travel to reach an X-ray detector;
    wherein said aperture is configured to limit the area of said sample which is exposed to said portion of primary X-ray photons;
    wherein said baffle plate is made of a material or materials which emit, when exposed to said primary X-ray photons, secondary X-ray photons having energy levels distinctly different than the energy levels of said secondary X-ray photons emitted from said sample;
    wherein said X-ray detector has a sensing face oriented toward said sample and is configured to receive said portion of secondary X-ray photons;
    a clamp configured to hold said sample and configured to precisely move said sample relative to said aperture so as to precisely adjust the area and location of said sample which is exposed to said portion of primary X-ray photons;
    a vacuum chamber containing said sample holder, said two radioisotopic X-ray sources, said baffle plate, and said sensing face; and
    a sample access port.

12. The apparatus as recited in claim 11, wherein said X-ray detector comprises a lithium-drifted silicon detector.

13. The apparatus as recited in claim 12, further comprising a liquid nitrogen dewar to hold liquid nitrogen used to cool said lithium-drifted silicon detector.

14. The apparatus as recited in claim 12, wherein said sample access port is located in an exposed surface of the vacuum chamber, wherein said sample holder is positioned on the underside of said sample access port such that the exposed surface of said sample is oriented downward during use.

* * * * *